1120B2" /># United States Patent
Kim et al.

(10) Patent No.: US 11,771,120 B2
(45) Date of Patent: Oct. 3, 2023

(54) FUNCTIONAL CRYSTALLINE SWEETENER

(71) Applicant: SAMYANG CORPORATION, Seoul (KR)

(72) Inventors: Go-Eun Kim, Gwangju-si (KR); Ji Won Park, Suwon-si (KR); Sung Won Park, Yongin-si (KR); Kyung-Hun Ryu, Seongnam-si (KR); Chong Jin Park, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 531 days.

(21) Appl. No.: 16/620,947

(22) PCT Filed: Feb. 12, 2018

(86) PCT No.: PCT/KR2018/001830
§ 371 (c)(1),
(2) Date: Dec. 10, 2019

(87) PCT Pub. No.: WO2019/004555
PCT Pub. Date: Jan. 3, 2019

(65) Prior Publication Data
US 2020/0196648 A1    Jun. 25, 2020

(30) Foreign Application Priority Data

Jun. 30, 2017  (KR) .................. 10-2017-0083906
Dec. 29, 2017  (KR) .................. 10-2017-0184905

(51) Int. Cl.
*A23L 27/30*    (2016.01)
*C07H 3/02*    (2006.01)

(52) U.S. Cl.
CPC .............. *A23L 27/33* (2016.08); *C07H 3/02* (2013.01); *C07B 2200/13* (2013.01)

(58) Field of Classification Search
None
See application file for complete search history.

(56) References Cited

U.S. PATENT DOCUMENTS

2017/0313734 A1 * 11/2017 Kim .................. B01D 9/0036
2018/0179604 A1    6/2018 Kim et al.

FOREIGN PATENT DOCUMENTS

| CN | 106480125 | 3/2017 |
|---|---|---|
| EP | 3210478 | 8/2017 |
| JP | 2001-011090 | 1/2001 |
| JP | 2005-263670 | 9/2005 |
| JP | 2011-206054 | 10/2011 |
| JP | 2012-232908 | 11/2012 |
| JP | 2013-082639 | 5/2013 |
| KR | 10-2011-0108185 | 10/2011 |
| KR | 10-2016-0046143 | 4/2016 |
| KR | 101617379 | * 4/2016 |
| KR | 10-1617379 | 5/2016 |
| KR | 10-2016-0062349 | 6/2016 |
| KR | 10-2017-0032899 | 3/2017 |
| KR | 10-2017-0072849 | 6/2017 |
| WO | 2016-012854 | 1/2016 |
| WO | 2016-064087 | 4/2016 |
| WO | 2016-182235 | 11/2016 |
| WO | 2017-029244 | 2/2017 |

OTHER PUBLICATIONS

Decision of Refusal in Japanese Patent Application No. 2019-569276, dated Jul. 26, 2021. (Year: 2021).*
Minna Hurtta et al, Melting behaviour of D-sucrose, D-glucose and D-fructose Carbohydrate Research 339 (2004) 2267-2273.
KIPO, PCT Search Report & Written Opinion of PCT/KR2018/001830 dated Jul. 2, 2018.
Landis W. Doner, "Isomerization of d-fructose by base: Liquid-chromatographic evaluation and the isolation of d-psicose", Carbohydrate Research, Pergamon, GB, vol. 70, No. 2, pp. 209-216.
EPO, Extended European Search Report of EP 18824244.0 dated Feb. 26, 2021.

* cited by examiner

*Primary Examiner* — Layla D Berry
(74) *Attorney, Agent, or Firm* — LEX IP MEISTER, PLLC (57) ABSTRACT

The present invention relates to functional saccharides having specific crystallinity, a method for preparing thereof, and a functional sweetener comprising the crystalline saccharides.

12 Claims, 4 Drawing Sheets

FUNCTIONAL CRYSTALLINE SWEETENER

TECHNICAL FIELD

The present invention relates to functional saccharides having specific crystallinity, a method for preparing thereof, and a functional sweetener comprising the crystalline saccharides.

BACKGROUND ART

General saccharides represented by sugar and starch sugar form the biggest market of about 65 trillion won in the world, but as consumer's needs for health-oriented functional and premium products are strengthened around the world, the market of functional sweeteners such as sugar alcohols including xylitol, oligosaccharides including fructooligosaccharide, functional saccharides including crystalline fructose, and sweeteners including sucralose or aspartame, etc. has been grown.

The sweetener is the generic term for seasoning and food additives providing sweet taste. Sugar, glucose, fructose, etc. among numerous sweeteners are distributed the most widely as natural components, and are the most widely used for preparing processed food. However, as the negative aspects of sugar such as cavity, obesity, diabetes, etc. become more prominent, the alternative functional sweetener for sugar have been received attention worldwide.

Recently, there is an allulose as an alternative saccharide which can substitute for sugar or fructose as a functional sweetener. The allulose can be prepared by chemical or biological methods, but the processes of purification and concentration are required, since allulose is contained at a low amount of the product. However, as the concentrated syrup has a limited application, the need for crystalline powder is high. It is difficult to crystallize the allulose due to its low crystallinity.

In addition, since the crystallization is performed after increasing the purity of D-allulose due to its low conversion rate, in case that the allulose is produced according to the biological method using an allulose converting enzyme or a strain producing the enzyme. There are unsolved problems left for purification process or purification yield, crystallization yield, etc., when D-allulose is intended for even the industrial use.

DISCLOSURE

Technical Problem

The purpose of the present invention is to provide a specific crystalline allulose, and a method for preparing the crystalline allulose with high yield and high purity.

In addition, the purpose of the present invention is to provide a sweetener including the crystalline allulose, and various food and beverages in which the sweetener is applied.

Technical Solution

The present invention provides a specific crystalline allulose, a method for preparing the crystalline allulose with high yield and high purity, and various uses of the specific crystalline allulose.

The allulose crystal according to one embodiment of the present invention may be an allulose crystal having a peak at angles of diffraction (2θ) of 15.24, 18.78, and 30.84±0.2° in the X-ray spectroscopy. In one embodiment of the present invention, the X-ray spectroscopy may be the an allulose crystal having a peak at angles of diffraction (2θ) of 15.24, 18.78, 30.84 and 28.37±0.2°, or an X-ray spectroscopy which has a peak at angles of diffraction (2θ) of 15.24, 18.78, 30.84 and 47.06±0.2°. The peaks having angles of diffraction in the X-ray spectroscopy of the allulose crystal shows the higher major peaks (Relative Intensity %) and morphology-specific peaks that are selected from the result of X-ray diffraction analysis.

The allulose crystal according to one embodiment of the present invention may have a Tm of 125.8° C.±5° C. or an enthalpy of melting (ΔH) from 200 to 220 J/g according to a differential scanning calorimetric analysis, and the Tm may be 125.8° C.±3° C.

The ratio of long diameter length (micrometer) to short diameter of the crystal (=long diameter/short diameter) of the allulose crystal according to one embodiment of the present invention may be 1.0 to 8.0.

The allulose crystal according to one embodiment of the present invention may be an allulose crystal having one or more characteristics selected from the group consisting of the following (1) to (5):

(1) a peak at angles of diffraction (2θ) of 15.24, 18.78, and 30.84±0.2° in the X-ray spectroscopy, (2) a Tm temperature of 125.8° C.±5° C. according to a differential scanning calorimetry analysis (DSC), (3) an enthalpy of melting (ΔH) of 200 to 220 J/g according to a differential scanning calorimetry analysis, (4) a mean long diameter of 350 μm or more, preferably 350 to 2,000 μm, and (5) a ratio of long diameter length (micrometer) to short diameter of the crystal (=long diameter/short diameter) in the range of 1.0 to 8.0.

An additional embodiment of the present invention relates to a sweetener composition comprising the allulose crystal having one or more characteristics selected from the group consisting of the characteristics (1) to (5). Another embodiment of the present invention includes food, beverages, feed for stocks, drugs, or cosmetics comprising the allulose crystal.

Hereinafter, the present invention will be described in more detail.

The allulose crystal according to one embodiment of the present invention may be an allulose crystal having one or more characteristics selected from the group consisting of the following (1) to (5):

(1) an X-ray spectroscopy which has a peak at angles of diffraction (2θ) of 15.24, 18.78, and 30.84±0.2° in the X-ray spectroscopy, (2) a Tm temperature of 125.8° C.±5° C. according to a differential scanning calorimetry analysis (DSC), (3) an enthalpy of melting (ΔH) of 200 to 220 J/g according to a differential scanning calorimetry analysis, (4) a mean long diameter of 350 μm or more, 350 to 2,000 μm, and (5) a ratio of long diameter length (micrometer) to short diameter of the crystal (=long diameter/short diameter) in the range of 1.0 to 8.0.

The allulose crystal according to the present invention may be obtained by various crystallization methods, for example, the characteristics may be measured with allulose crystals prepared by a cooling method.

According to the X-ray spectroscopy analysis of powder of allulose crystal in the present invention, the allulose crystal may have an X-ray spectroscopy which has a peak at angles of diffraction (2θ) of 15.24, 18.78, and 30.84±0.2° in the X-ray spectroscopy. Preferably, the crystal may have an X-ray spectroscopy which has a peak at angles of diffraction (2θ) of 15.24, 18.78, 30.84 and 28.37±0.2°, at angles of diffraction (2θ) of 15.24, 18.78, 30.84 and 31.87±0.2°, or at angles of diffraction (2θ) of 15.24, 18.78, 30.84 and 47.06±0.2°. More specifically, the X-ray spectroscopy may have a peak at angles of diffraction (2θ) of 15.24, 18.78, 30.84, 27.37, 47.06 and 31.87±0.2° in the X-ray spectroscopy.

The diffraction peak values in the aforementioned diffraction angles (2θ) may represent a little error of measurement due to measuring device or measuring conditions, etc. Specifically, the error of measurement may be in the range of ±0.2°, preferably ±0.1°, more preferably ±0.06°.

The allulose crystal according to the present invention may be analyzed by thermal analytical methods, specifically the differential scanning calorimetry analysis (DSC). By the DSC analysis, the melting temperature (Tm) of the allulose crystal according to the present invention may be 125.8° C.±5° C., preferably ±3.0° C., or more preferably ±1.0° C. The allulose crystal has an enthalpy of melting (ΔH) by the DSC analysis of 200 to 220 J/g, for example, 212.7 J/g. The differential scanning calorimetry analysis (DSC) is operated according to the temperature gradient, and measures the energy provided to maintain the temperature increase of allulose powder sample. It could be predicted that the higher the thermal capacity is in the DSC analysis of crystal, the more difficult it is dissolved, and as the thermal capacity is higher and the width of endothermic peak are more narrow, the crystal is formed more homogeneous and the harder.

The allulose crystal according to the present invention, the mean short diameter or minor diameter of crystal may be 50 to 1,000 μm, or preferably 50 to 500 μm, and the mean long diameter may be 350 μm or higher, preferably 350 to 2,000 μm, or more preferably 400 μm to 2,000 μm.

In addition, the ratio of long diameter length (micrometer) to short diameter (=long diameter/short diameter) of allulose crystal according to the present invention may be 1.0 to 8.0, 1.0 to 6.9, 1.0 to 6.0, 1.0 to 5.5, 1.0 to 5.0, 1.1 to 8.0, 1.1 to 6.9, 1.1 to 6.0, 1.1 to 5.5, 1.1 to 5.0, 1.3 to 8.0, 1.3 to 6.9, 1.3 to 6.0, 1.3 to 5.5, 1.3 to 5.0, 1.5 to 8.0, 1.1 to 6.9, 1.5 to 6.0, 1.5 to 5.5, 1.5 to 5.0, 2.0 to 8.0, 2.0 to 6.9, 2.0 to 6.0, 2.0 to 5.5, or 2.0 to 5.0.

By the result of XRD pattern analysis for allulose crystal powder of the present invention, the allulose crystal is a pure crystal particle, and has a structure of rectangle hexahedron or close thereto. It is more preferable that the uniformity and solidity of crystal are increased, as the crystal structure of the present invention closes to a cubic system.

In addition, as the allulose crystal prepared in the crystallization process is more homogeneous, the strength of crystal is increased and particle breakage is minimized, thereby making the particle-size distribution be homogeneous. Therefore, the flowability of allulose crystal may be enhanced. On the other hand, when the uniformity is lower, it may be micronized due to the breakage of crystal particles in the drying and transferring process, and may be relatively easily dissolved, thereby affecting the quality of product negatively.

Herein, the term "purity of crystal" means the purity of allulose crystal. The properties including the purity of crystal in the present invention may be obtained by the methods such as for example, X-ray powder diffraction analysis, differential scanning calorimetry (DSC) analysis, infrared spectroscopic (FTIR) analysis, HPLC analysis, LC/MS analysis, etc., and the purity may be specifically analyzed by HPLC chromatography.

The purity of crystal in the present invention may be 70 wt % or higher, preferably, 80 wt % or higher, more preferably, 90 wt % or higher, more preferably 95 wt % or higher, or the most preferably, 98 wt % or higher. It is preferable to achieve the range of purity for quality guarantee.

The allulose crystal of the present invention has higher flowability than micronized powder, and it is stable during storage due to low caking and easily distributed and treated. In addition, the allulose powder has lower calories than sugar, and similar sweet property to sugar, and thus it may be used easily and advantageously for preparation of mixed sweeteners, solid mixed sweeteners, chocolate, chewing gum, instant juice, instant soup, granules, tablets, etc. Furthermore, the allulose crystal powder may be used by being contained in various compositions such as food and beverages, favorite dainty, feed, cosmetics, drugs, etc., and the method of containing saccharides may be properly selected among publicly known methods such as blending, mixing, dissolving, melting, soaking, penetrating, scattering, spreading, coating, spraying, injecting, crystallizing, solidifying and the like as a process of completing the manufacture of the product.

Specific one embodiment of the present invention may provide a sweetener composition comprising the allulose crystal powder. The sweetener composition may comprise various contents of allulose crystal powders. The sweetener composition may further comprise one or more selected from the group consisting of high-intensity sweetener, monosaccharides except for allulose, disaccharides, sugar-alcohols, dietary fibers and oligosaccharides.

For example, the monosaccharide and disaccharide may be one or more selected from the group consisting of allose, deoxyribose, erythrulose, galactose, idose, mannose, ribose, sorbose, tagatose, erythrose, fuculose, gentiobiose, gentiobiulose, isomaltose, isomaltulose, kojibiose, lactulose, altrose, laminaribiose, arabinose, leucrose, fucose, ramnose, sorbose, maltulose, mannobiose, mannosucrose, melezitose, melibiose, melibiulose, nigerose, raffinose, rutinose, rutinulose, stachyose, treose, trehalose, trehalulose, turanose, xylobiose, fructose, glucose and allulose.

The sugar-alcohol may be one or more kinds selected from the group consisting of xylitol, maltitol, erythritol, mannitol, lactitol, inositol and sorbitol. The dietary fiber may be water soluble dietary fiber, and the dietary fiber may be one or more selected from the group consisting of polydextrose, non-digestible maltodextrin and pectin. The oligosaccharide may be one or more selected from the group consisting of fructooilgosaccharide, isomaltooligosaccharide, maltooligosaccharide, and galactooligosaccharide.

The high-intensity sweetener may be one or more selected from the group consisting of aspartame, acesulfame potassium, sodium cyclamate, sodium saccharin, sucralose, stevia sweeteners (steviol glycoside, enzyme-treated stevia), dulcin, thaumatin, neotame, rebaudioside and monellin.

The preparation method of allulose crystal according to the present invention may be performed by various methods, and preferably may be performed by a cooling method. As one embodiment of the cooling method according to the present invention, the preparation method of allulose crystal may comprise a step of producing a crystal nucleus by slowly stirring at the temperature of 20 to 40° C., or 30 to 40° C., for example, 35° C., an allulose solution comprising 90 wt % or higher of allulose and having 60 to 85 Brix, and a step of growing a crystal by lowering the temperature of the solution. For example, the crystal may be produced by inducing supersaturated state with cooling the temperature of allulose solution to the range of 35 to 10° C. It is preferably to maintain the cooling rate as 0.01 to 20° C./min. When the cooling rate is low, the time for forming a co-crystal is long, thereby decreasing the productivity. When the cooling rate is high, a small particle size of crystal is formed, thereby making the recovery of crystal be difficult.

The preparation method of allulose crystal may comprise a step of producing a crystal nucleus in an allulose solution comprising 90 wt % or higher of allulose and having 60 to 85 Brix and 1,000 uS/cm or lower of conductivity, and a step of growing a crystal by lowering the temperature of the solution. Specifically, the preparation method of allulose crystal may comprise a step of producing a crystal nucleus by slowly stirring at the temperature of 35° C. an allulose solution comprising 90 wt % or higher of allulose and having 80 to 83 Brix, and a step of growing a crystal by lowering the temperature of the solution. The method may be further comprise a step of re-dissolving microcrystals produced during cooling by increasing the temperature of solution in the range of 20° C. to 40° C., preferably 30 to 35° C., at one or more times. The preparation method of allulose crystal may further comprise a step of adding a seed. Each seed-addition step and re-dissolving step may be included selectively in the preparation method of allulose crystal, or both steps may be included.

The allulose solution used for crystallization may be a high-purity allulose solution comprising 90 wt % or higher of allulose, for example, 95 wt % or higher. The viscosity of the composition may be 2 cps to 200 cps at the temperature of 45° C., and the conductivity may be 1000 uS/cm or lower, for example, 0.01 to 1000 uS/cm, preferably 30 uS/cm or lower, for example 0.1 to 30 uS/cm. The lower conductivity of composition used for allulose crystallization is preferably for crystallization. The allulose solution for crystallization may has the solid content of 60 to 85 Brix, for example, higher than 60 Brix to 80 Brix, 65 to 85 Brix, 65 to 80 Brix, or 68 to 85 Brix.

In common cases, it is known that the bigger the size of allulose crystal is, the better the properties are and the more the use convenience is increased. In order to prepare the big size of crystal, a seed crystallization and a main crystallization divided by a transferring process are required. However, the crystallization process of the present invention can easily prepare a crystal with relatively big size at high yield by only one step process.

In addition, the crystallization process may perform a step of dissolving a microcrystal by increasing the temperature of solution to the ranges of 30 to 35° C., in order to redissolve the microcrystal produced in the cooling of the crystal growing step. In the crystallization process of the present invention, the crystal growing step and microcrystal dissolving step may be repeated and carried out one or more times.

In the process for preparing the crystal, a seed may be further added for a purpose of increasing the production rate and the size of crystal.

In one embodiment according to the present invention, the allulose crystal may be prepared by stirring an allulose solution comprising 90 wt % or higher of allulose at 60 to 85 Brix of total solid content at the temperature of 20 to 40° C., preferably 30 to 40° C., or for example, 35° C., to produce a small amount of crystal nucleus, and then, growing the crystal by cooling the temperature of solution to 10° C., by 1° C. per hour. Optionally, the preparation method of allulose crystal further includes a step of dissolving the microcrystal by increasing the temperature of solution to the range of 30 to 35° C. for redissolving the microcrystal produced during the cooling, one or more times.

In one specific embodiment of the present invention, the method for preparing the allulose crystal may comprise a step of the secondary ion purification of allulose fraction obtained in the SMB chromatography separation process, a step of concentrating the ion purified allulose fraction, a step of obtaining the allulose crystal by crystallization of allulose from the concentrates, and optionally, may further comprise recovering the allulose crystal, washing and drying.

The specific embodiment of preparation of allulose crystal may comprise the primary ion purification, SMB chromatography separation, the secondary ion purification, concentration and crystallization steps, and selectively, may perform an activated carbon treating step, an ion purification step, or both of activated carbon treating step and ion purification step for allulose conversion products.

The method for preparing the allulose crystal according to the present invention may include the method of crystallizing the allulose by controlling the temperature and concentration of allulose concentrate solution, and specifically, the supersaturated condition required for crystallization may be maintained by reducing the temperature of allulose solution or changing the concentration of D-allulose in the D-allulose solution. In one specific embodiment of the present invention, the crystallization progress may be monitored by observing the sample collected at a constant interval in the crystallization step with the naked eye or microscope, or analyzing the concentration of saccharide in the supernatant collected by centrifugation of sample, and the temperature or concentration of D-allulose may be controlled on the basis of the analyzing result. For preparing the allulose crystal, when the allulose concentrate solution is cooled and crystallized, the crystal growth may be induced by performing the increase and the decrease of temperature repeatedly, after rapidly cooling to the temperature range of 10 to 25° C. with a heat exchanger.

The method for preparing the allulose crystal according to the present invention may further comprise a step of recovering the allulose crystal in the crystallization step by various solid-liquid separation methods, for example, centrifugation, a step of washing with deionized water, and a step of drying. The drying step may be performed in a fluidized bed drier or vacuum drier, but not limited thereto. The allulose content contained in the allulose crystal may be 94 wt % or higher, 95 wt % or higher 96 wt % or higher, 97 wt % or higher, 98 wt % or higher, or 99 wt % or higher, based on 100 wt % of solid total content.

Effect of the Invention

The allulose crystal and the method for preparing thereof according to the present invention can provide the allulose crystal with high yield and high purity, and the allulose crystal is contained in a sweetener to be applied for various food and beverages.

DETAILED DESCRIPTION OF THE EMBODIMENTS

The present invention will be described in more detail by the following examples. However, the following examples are desirable examples of the present invention, and the present invention is not limited thereto.

Example 1: Allulose Crystal Preparation

The high-purity allulose syrup including 94.6 wt % of allulose based on the solid content of 100 wt % was concentrated, to prepare the allulose syrup for crystallization having the conductivity of 8 uS/cm. The prepared allulose syrup for crystallization was cooled slowly from the temperature of 35° C. of the supersaturated state to the temperature of 10° C., to grow the crystal. At this time, a small amount of crystal nucleus were formed by slowly stirring at the temperature of 35° C. with the addition of allulose seed, and the crystal was grown by decreasing the temperature by 1° C. per hour. In the crystal growing step, the microcrystal produced in the cooling was re-dissolved by increasing the temperature of solution to the ranges of 30 to 35° C. The crystal growing process and microcrystal dissolving process were repeated one or more times to perform the crystallization. The prepared allulose crystals were recovered by removing the mother liquor with centrifuge dehydration and the recovered crystals in the primary crystallization were washed with cooling water and dried.

The obtained primary crystals were dissolved in water to prepare the allulose solution of 81.6 Bx and 99.5 wt % of allulose based on the solid content of 100 wt %.

The secondary crystallization process was performed with the prepared allulose-dissolved solution according to the substantially same method as the primary crystallization method. The prepared allulose crystals were recovered by removing the mother liquor with centrifuge dehydration and the recovered crystals in the secondary crystallization were washed with cooling water and dried.

For the purity of prepared allulose crystal, the following HPLC analysis was carried out with the following analysis conditions:
Analysis column: Biolad Aminex HPX-87C column
Mobile phase: water
Flow rate: 0.6 ml/min
Column temperature: 80° C.
Detector: RI detector As the result of HLPC analysis, the purity of allulose in the alluose crystal prepared in Example 1 was 99.8 wt %, and the crystal yield was 62.5%. The crystal yield was represented as a percentage of the weight of recovered allulose crystal powder to the weight of solid of raw allulose syrup used for crystallization.

Example 2: Allulose Crystal Preparation

The high-purity allulose syrup comprising 94.6 wt % of allulose based on the solid content of 100 wt % was concentrated to 82.6 Bx, thereby preparing the allulose syrup for crystallization having the conductivity of 16 uS/cm. The prepared allulose syrup for crystallization was cooled slowly from the temperature of 35° C. at the supersaturated state to the temperature of 10° C., to grow the crystal. At this time, a small amount of crystal nucleus were formed by slowly stirring at the temperature of 35° C. with the addition of allulose seed, and the crystal was grown by decreasing the temperature by 1° C. per hour. In the crystal growing step, the microcrystal produced in the cooling was re-dissolved by increasing the temperature of solution to the ranges of 30 to 35° C. The crystal growing process and microcrystal dissolving process were repeated one or more times to perform the crystallization. The prepared allulose crystals were recovered by removing the mother liquor with centrifuge dehydration and the recovered crystals in the primary crystallization were washed with cooling water and dried.

The purity analysis of prepared allulose crystal was conducted by HPLC analysis with the same method as Example 1, and the allulose purity of alluose crystal prepared in Example 2 was 99.6 wt %, and the crystal yield was 52.8%.

Example 3: Allulose Crystal Preparation

The high-purity allulose syrup comprising 91.5 wt % of allulose based on the solid content of 100 wt % was concentrated to 81.2 Bx, thereby preparing the allulose syrup for crystallization having the conductivity of 21 uS/cm. The prepared allulose syrup for crystallization was cooled slowly from the temperature of 35° C. at the supersaturated state to the temperature of 10° C., to grow the crystal. The prepared allulose syrup for crystallization was cooled slowly from the temperature of 35° C. at the supersaturated state to the temperature of 10° C., to grow the crystal. At this time, a small amount of crystal nucleus were formed by slowly stirring at the temperature of 35° C. with the addition of allulose seed, and the crystal was grown by decreasing the temperature by 1° C. per hour. In the crystal growing step, the microcrystal produced in the cooling was re-dissolved by increasing the temperature of solution to the ranges of 30 to 35° C. The crystal growing process and microcrystal dissolving process were repeated one or more times to perform the crystallization. The prepared allulose crystals were recovered by removing the mother liquor with centrifuge dehydration and the recovered crystals in the primary crystallization were washed with cooling water and dried.

The purity analysis of prepared allulose crystal was conducted by HPLC analysis with the same method as Example 1, and the purity of allulose of alluose crystal prepared in Example 3 was 99.6 wt %, and the crystal yield was 34%.

According to the preparation of the allulose crystals of Examples 1 to 3, since other components except allulose acted as impurities disturbing the crystal growth of pure allulose, as the allulose purity used as a raw material for crystallization was low, the difference in crystal yields occurred depending on the allulose purity of the raw material for crystallization. Specifically, the crystal obtained by twice crystallization processes of allulose syrup in Example 1 exhibited higher purity and crystal yield of allulose crystal, than Example 2 performing one crystallization process. Example 1 and Example 2 exhibited higher purity and crystal yield of allulose crystal, than Example 3 using relatively low purity of the raw material for crystallization.

Example 4: Analysis of Allulose Crystal Characteristics 4-1: Analysis of Crystal Particle Size Distribution The particle size distribution of allulose crystal obtained in Example 1 and Example 3 was confirmed by using standard sieves by Mesh. The Mesh sizes of standard sieves were 20, 30, 40, 60, 80, 100 mesh, and the size distribution of crystal particle was measured by the hole-sizes of standard sieves.

The hole-sizes of standard sieves by each mesh were 850, 600, 425, 250, 180, and 150 μm. 100 g of each sample was collected and put in standard sieves by mesh size, and passed through the standard sieves by adding vibration. The percentage values were described in Table 1 by measuring the weight of samples remained in sieves by each mesh size. In the following Table 1, the particle size distribution by each mesh was represented by wt % of particle with numerical values.

TABLE 1

| Mesh size (mesh) | Particle size (μm) | Example 1 | Example 3 |
| --- | --- | --- | --- |
| 100 mesh pass | ≤150 | 0.9 | 2 |
| 100 mesh ↑ | 150< | 2.6 | 3.2 |
| 80 mesh ↑ | 180< | 5.9 | 15.5 |
| 60 mesh ↑ | 250< | 20.2 | 25.9 |
| 40 mesh ↑ | 425< | 70 | 36.9 |
| 30 mesh ↑ | 600< | 0.4 | 16.6 |
| 20 mesh ↑ | 850< | 0 | 0 |

As shown in the Table 1, it was confirmed that the allulose crystal of Example 1 exhibited very narrow distribution converging into 90.2 wt % of the particle distribution, and the allulose crystal of Example 3 exhibited the most distribution in 40↑, but the particle distribution was widely spread as evenly distributed in 80↑, 60↑, 40↑, and 30↑. It was confirmed that the hard crystal particle having low ratio of long diameter/short diameter as Example 1 had relatively low content of micronized products and uniform distribution of particle size. In addition, the particle having high ratio of long diameter/short diameter and low homogeneity may be micronized by particle breakage in the drying and transferring processes and the particle size may be heterogeneous, thereby having the wide range of particle size distribution.

4-2: Analysis of Crystal Form and Crystal Particle Size

Figure 1:
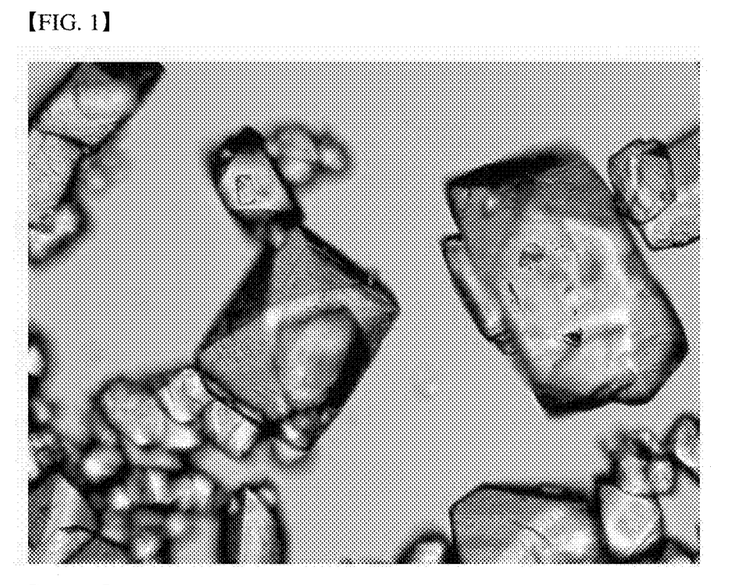
FIG. 1 to FIG. 3 are optical microscopic photographs of allulose powders obtained from Examples 1 to 3 of the present invention, measured at magnification×100.
Figure 2:
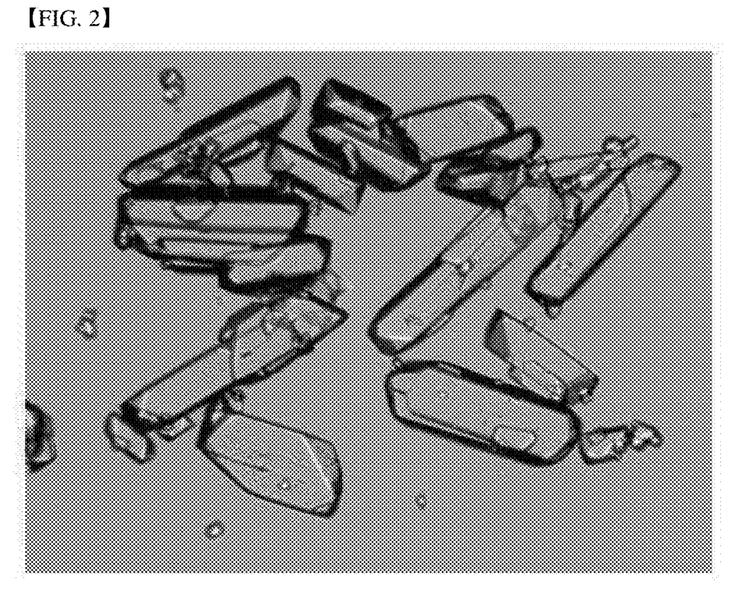
Figure 3:
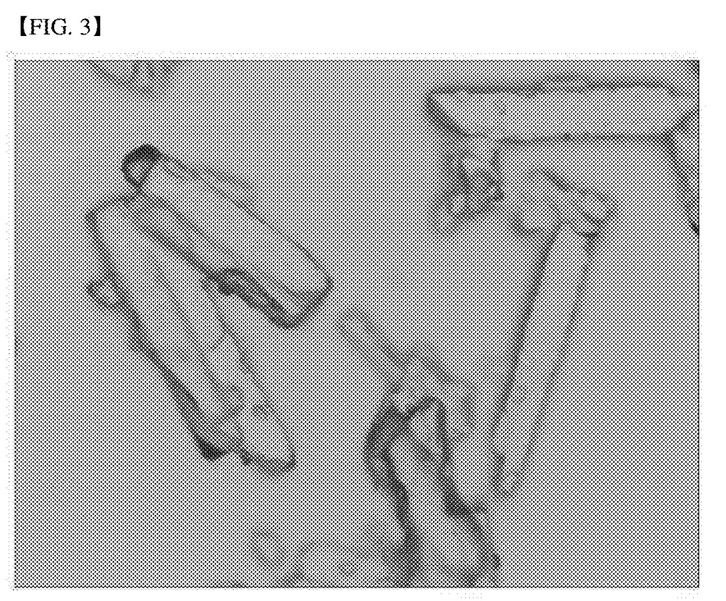

The optical microscopic photographs of allulose crystals obtained in Examples 1 to 3 measured by magnification ×100 were shown in FIG. 1 to FIG. 3. The scanning microscopic photographs of allulose crystals obtained in Examples 1 to 3 measured by magnification ×100 were shown in FIG. 4 to FIG. 6.

In addition, the long diameters (height) and short diameters (width) for 9 samples of allulose crystals obtained in Examples 1 to 3 were measured, and the particle diameter ratio (=long diameter/short diameter) was obtained and shown in the following Table 1. Specifically, for 5 crystals, the ratio of length of long diameter (μm) was shown, on the basis of short diameter length (μm) as 1.

TABLE 2

| Crystals | Example 1 | Example 2 | Example 3 |
| --- | --- | --- | --- |
| #1 | 1.3 | 6.2 | 3.8 |
| #2 | 1.5 | 2.1 | 11.1 |
| #3 | 1.2 | 4.4 | 12.7 |
| #4 | 1.2 | 3.0 | 6.5 |
| #5 | 2.1 | 5.2 | 5.3 |
| #6 | 1.7 | 3.3 | 8.5 |
| #7 | 1.7 | 5.5 | 8.3 |
| #8 | 1.4 | 4.1 | 6.4 |
| #9 | 2.4 | 4.5 | 5.4 |
| average | 1.6 | 4.3 | 7.6 |

Figure 4:
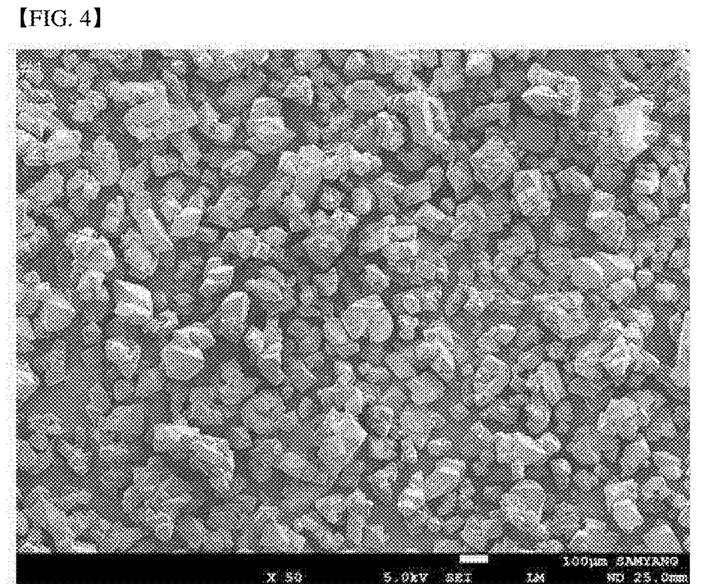
FIG. 4 to FIG. 6 are scanning electron microscopic (SEM) photographs of allulose powders obtained from Examples 1 to 3 of the present invention, measured at magnification×50.
Figure 5:
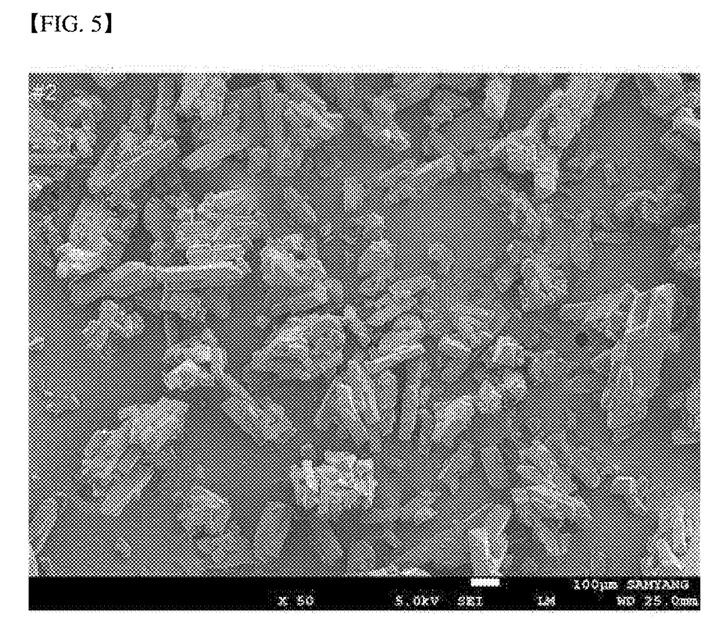
Figure 6:
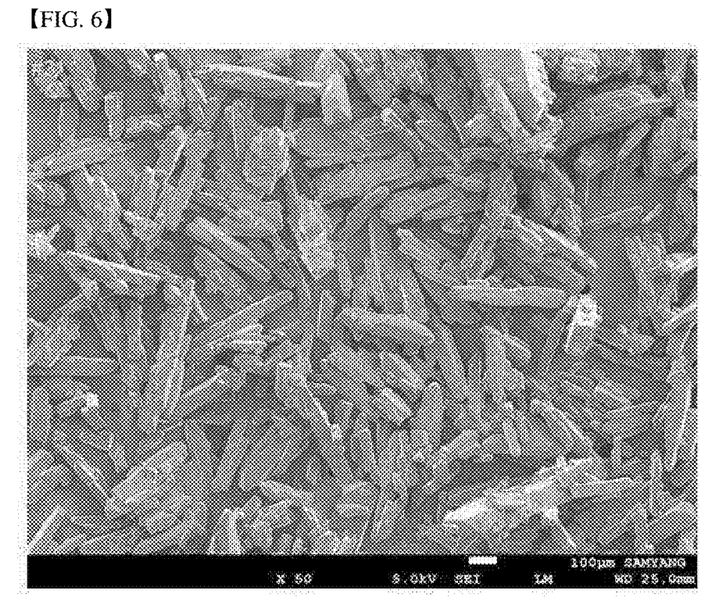

As shown in FIG. 4 to FIG. 6, the allulose crystal of the present invention had a rectangle hexahedron or crystal structure close thereto. The ratio of long diameter length (am) to the short diameter length (μm) of 1 of crystals in the Table 2 showed that average 1.6 in Example 1, average 4.3 in Example 2, and average 7.6 in Example 3, relatively. Example 1 formed the crystal form of rhombic system close to quadrate as each crystal side was grown homogeneously, than crystals of Example 2 and Example 3. In addition, it was confirmed that the ratio of long diameter/short diameter tended to be reduced, as the crystal side was grown homogenously. This was suggested that since other components except for allulose acted as impurities disrupting the crystal growth of pure allulose, as the allulose purity in raw material for crystallization was low, they affected the crystal shape.

Example 5: Differential Scanning Calorimetry (DSC) Analysis

The DSC analysis of allulose crystals obtained in Examples 1 to 3 was performed under the specific DSC analysis conditions.
Equipment name: DSC [differential scanning calorimetry]
Manufacturer: Perkin Elmer
Method: 30 to 250° C., 10° C./min temperature rising, N2 gas purge
(standard method: refer to ASTM D 3418)
The result of DSC analysis of allulose crystal was shown in the following Table 3.

TABLE 3

| Classification | Tm(° C.) | ΔH(J/g) |
| --- | --- | --- |
| Example 1 | 127.89 | 207.5 |
| Example 2 | 125.96 | 206.2 |
| Example 3 | 121.55 | 201.4 |

As the result of DSC analysis, the crystal in Example 1 had the highest Tm value, and the highest thermal capacity. It could be predicted that as the thermal capacity was higher in the DSC analysis of crystal, it was not easily dissolved, and as the thermal capacity was higher and the width of endothermic peak was narrower, the crystal was formed homogeneously and firmly. In consideration of thermal capacity and endothermic peak enthalpy values of Examples 1 to 3, it was confirmed that the crystal of Example 1 was formed relatively more homogeneously and firmly.

Example 6: Infrared Adsorption (IR) Spectrum Analysis

Figure 7:
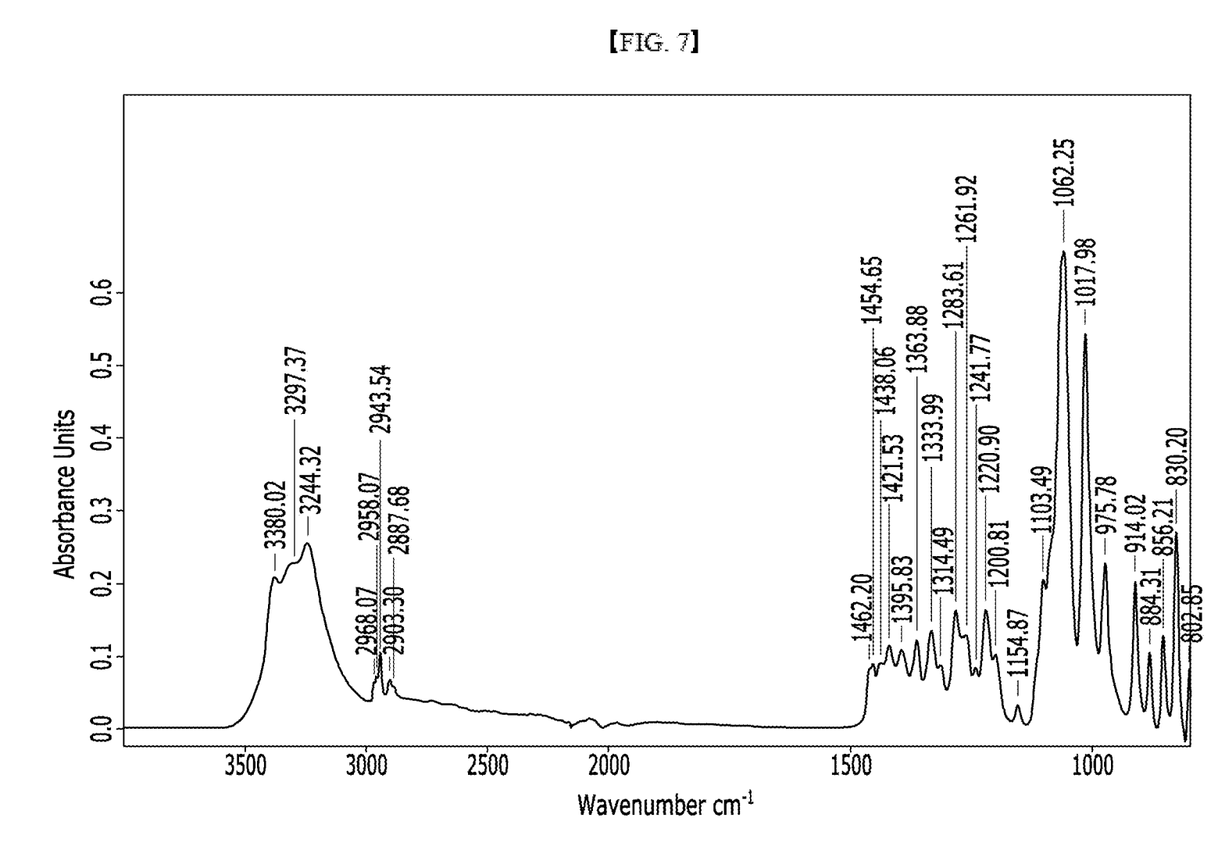
FIG. 7 is the infrared spectroscopic analysis (IR) spectrum of allulose crystals obtained from Examples 1 to 3 of the present invention.

To confirm the prepared allulose crystal, the infrared adsorption (IR) spectrum analysis was carried out for the crystals of Examples 1 to 3, under the measuring conditions.
Analysis equipment: TENSOR II with Platinum ATR, manufacturer; Bruker (German)
Detector: highly sensitive photovoltaic MCT detector with liquid nitrogen cooling.
Scan number of times: 64 scans at 20 kHz
Scan range: 800-4,000 $cm^{-1}$ and averaged at 4 cm-1 resolution.
According to the result of infrared adsorption (IR) spectrum analysis for the allulose crystal according to the present invention, the allulose crystal had unique structural characteristic as the allulose molecule included functional groups —OH, and C—O—C, C—C, C—OH, etc. in the allulose molecular structure. It demonstrated that the crystals of Examples 1 to 3 were identical allulose crystals. The IR analysis spectrum was shown in FIG. 7.

Example 7: X-Ray Diffraction (XRD) Analysis

The X-ray diffraction analysis was performed according to the following specific analysis conditions, for the allulose crystals obtained in Examples 1 to 3, and the result of X-ray diffraction analysis of allulose crystals obtained in Examples 1 to 3 was shown in Table 4 by selecting the higher (Relative Intensity %) five peaks and morphology specific peaks.

Analysis equipment: D/MAX-2200 Ultima/PC
Manufacturer: Rigaku International Corporation (Japan)
X-ray sauce system target: sealed tube Cu
Tube voltage: 45 kV/Tube current: 200 mA
Scan range: 5 to 80° 2θ
Step size: 0.01°
Scan speed: 5°/min

TABLE 4

| Crystal of Example 1 | | Crystal of Example 2 | | Crystal of Example 3 | |
|---|---|---|---|---|---|
| Angle 2-Theta degree | Relative Intensity % | Angle 2-Theta degree | Relative Intensity % | Angle 2-Theta degree | Relative Intensity % |
| 18.78 | 100.0 | 15.27 | 100.0 | 15.28 | 100.0 |
| 15.24 | 97.6 | 18.77 | 30.5 | 18.79 | 30.5 |
| 28.37 | 9.5 | 22.90 | 9.7 | 22.90 | 12.1 |
| 30.84 | 18.8 | 30.87 | 20.2 | 30.87 | 23.3 |
| 31.87 | 9.0 | 31.88 | 9.1 | 33.93 | 7.6 |
| 47.06 | 4.1 | 47.08 | 7.0 | 47.09 | 4.6 |

As shown in the Table 4, it was confirmed that the allulose crystal obtained in Example 1 had specific peaks in 15.24, 18.78 and 30.84; 15.24, 18.78, 30.84, and 28.37; or 15.24, 18.78, 30.84 and 31.87; of 2θ values in the powder X-ray spectroscopy.

In the X-ray spectroscopy, it was confirmed that the crystals of Examples 1 to 3 formed identical crystal lattice structure, as they had the same range of Angle 2-Theta degree values. There might be different orientation of crystal lattices, as the crystal of Example 1 had little different external crystal form from crystals of Examples 2 and 3, thereby causing the difference of Intensity % values.

Example 8: Measurement of Flowability of Allulose Crystal

To analyze the flowability of allulose crystal, the angles of repose of crystal powders of Example 1 and Example 3 were measured.

Specifically, the angles of repose were measured at 3 different points based on the slope covered with horizontal planes like mountains where it did not slide down by passing the crystal powders of Examples 1 and 3 through the funnel fixed at the constant height as 20 cm on the standard board which was a complete plane.

The angles of repose of crystal obtained in Example 1 was 42.6°, 43.3°, 42.2°±0.2° and the average value was 42.7±0.2°, and the angles of repose of crystal obtained in Example 3 was 46.0°, 45.3°, 46.2°±0.2° and the average value was 45.8°±0.2°. The repose angle is a shape made by natural falling of powder on the horizontal plane, and this largely affects the flowability. In common, when the angle of repose is small, the flowability of powder can be judged as good. As the result of measuring the angles of repose of sugar (average particle diameter 420 μm) and crystal fructose (average particle diameter 341 μm) with the same method as the method of measuring the angles of repose of allulose crystal, the average value of angle of repose of sugar was 41.2°±0.2°, and the average value of angle of repose of crystal fructose was 41.8°±0.2°. Compared to repose angles of sugar and crystalline fructose, the allulose crystal had the powder flowability being equivalent to their level.

The invention claimed is:

1. An allulose crystal having an X-ray spectrum which has a peak at angles of diffraction (2θ) of 15.24, 18.78, 30.84, and 31.87 in the X-ray spectroscopy, wherein each of four out of five highest peaks in relative intensity are located at the angles of diffraction (2θ)±0.2°, respectively.

2. The allulose crystal of claim 1, wherein the X-ray spectrum has a peak at angles of diffraction (2θ) of 15.24, 18.78, 30.84, 31.87 and 28.37±0.2° in the X-ray spectroscopy, wherein each of five highest peaks in relative intensity are located at the angles of diffraction (2θ)±0.2°, respectively.

3. The allulose crystal of claim 1, wherein the X-ray spectrum has a peak at angles of diffraction (2θ) of 15.24, 18.78, 30.84, 31.87 and 47.06±0.2° in the X-ray spectroscopy.

4. The allulose crystal of claim 1, wherein the X-ray spectrum has a peak at angles of diffraction (2θ) of 15.24, 18.78, 30.84, 28.37, 47.06 and 31.87±0.2° in the X-ray spectroscopy.

5. The allulose crystal of claim 1, wherein the allulose crystal has a Tm of 125.8° C.±5° C. or an enthalpy of melting (ΔH) from 200 to 220 J/g measured according to a differential scanning calorimetric analysis (DSC).

6. The allulose crystal of claim 5, wherein the Tm is a temperature of 125.8° C.±3° C.

7. The allulose crystal of claim 1, wherein the allulose crystal has 350 μm or higher of mean major diameter of crystal.

8. The allulose crystal of claim 1, wherein the ratio of major diameter length (micrometer) to minor diameter of the crystal (=major diameter/minor diameter) is in the range of 1.0 to 8.0.

9. The allulose crystal of claim 1, wherein the mean minor diameter of the crystal is 50 μm to 1,000 μm.

10. The allulose crystal of claim 1, wherein the allulose purity of crystal is 70 wt % or higher.

11. A sweetener composition comprising the allulose crystal according to claim 1.

12. The sweetener composition of claim 11, wherein the sweetener composition further comprises one or more selected from the group consisting of monosaccharides except for allulose, disaccharides, sugar-alcohols, dietary fibers and oligosaccharides.

* * * * *